US010245362B2

(12) United States Patent
Yomtov

(10) Patent No.: US 10,245,362 B2
(45) Date of Patent: Apr. 2, 2019

(54) BLOOD PUMP FOR TREATMENT OF BRADYCARDIA

(71) Applicant: HeartWare, Inc., Miami Lakes, FL (US)

(72) Inventor: Barry M. Yomtov, Marblehead, MA (US)

(73) Assignee: HeartWare, Inc., Miami Lakes, FL (US)

(*) Notice: Subject to any disclaimer, the term of this patent is extended or adjusted under 35 U.S.C. 154(b) by 0 days.

(21) Appl. No.: 15/551,170

(22) PCT Filed: Feb. 9, 2016

(86) PCT No.: PCT/US2016/017148
§ 371 (c)(1),
(2) Date: Aug. 15, 2017

(87) PCT Pub. No.: WO2016/137743
PCT Pub. Date: Sep. 1, 2016

(65) Prior Publication Data
US 2018/0021496 A1    Jan. 25, 2018

Related U.S. Application Data

(60) Provisional application No. 62/119,895, filed on Feb. 24, 2015.

(51) Int. Cl.
*A61M 1/10* (2006.01)
*A61M 1/12* (2006.01)
*A61N 1/362* (2006.01)

(52) U.S. Cl.
CPC .......... *A61M 1/1086* (2013.01); *A61M 1/101* (2013.01); *A61M 1/1005* (2014.02);
(Continued)

(58) Field of Classification Search
None
See application file for complete search history.

(56) References Cited

U.S. PATENT DOCUMENTS 4,250,872 A * 2/1981 Tamari ................ A61M 1/1005
                                                                     417/385
4,627,419 A * 12/1986 Hills ................... A61M 1/1065
                                                                   128/DIG. 12

(Continued)

OTHER PUBLICATIONS

International Preliminary Report on Patentability, dated Aug. 4, 2017, for corresponding International Application No. PCT/US2016/017148; International Filing Date: Feb. 9, 2016 consisting of 12 pages.

(Continued)

*Primary Examiner* — Kennedy Schaetzle
(74) *Attorney, Agent, or Firm* — Christopher & Weisberg, P.A.

(57) ABSTRACT

A ventricular assist device incorporating a rotary pump (3) such as a rotary impeller pump implantable in fluid communication with a ventricle and an artery to assist blood flow from the ventricle to the artery. The device includes a pump drive circuit (6) supplying power to the pump, one or more sensors (10) for sensing one or more electrophysiological signals such as electrogram signals in and a signal processing circuit (23) connected to the sensors and to the pump drive circuit. The signal processing circuit is operative to detect the sensor signals and control power supplied to the pump from the pump drive circuit so that the pump runs in a normal sinus rhythm mode, with a varying speed synchronized with the cardiac cycle. When a bradycardia arrhythmia is detected, the pump drive circuit may also nm the pump in a sinus bradycardia mode or a heart block mode different from the normal sinus rhythm mode.

15 Claims, 5 Drawing Sheets

(52) U.S. Cl.
CPC ......... *A61M 1/122* (2014.02); *A61M 2205/33* (2013.01); *A61M 2205/3303* (2013.01); *A61M 2205/3334* (2013.01); *A61M 2205/3365* (2013.01); *A61M 2230/04* (2013.01); *A61N 1/3627* (2013.01)

(56) References Cited

U.S. PATENT DOCUMENTS

| | | | |
|---|---|---|---|
| 4,957,504 A | | 9/1990 | Chardack |
| 5,458,468 A | * | 10/1995 | Ye .................. A61F 2/2406 417/395 |
| 6,327,499 B1 | | 12/2001 | Alt |
| 7,001,354 B2 | * | 2/2006 | Suzuki ............. A61M 1/3613 600/17 |
| 8,864,644 B2 | * | 10/2014 | Yomtov ............. A61M 1/10 600/16 |
| 2004/0260214 A1 | * | 12/2004 | Echt ............... A61H 23/0245 601/46 |
| 2011/0178361 A1 | | 7/2011 | Yomtov |
| 2014/0343445 A1 | | 11/2014 | Scholz et al. |

OTHER PUBLICATIONS

International Search Report and Written Opinion dated Apr. 29, 2016, for corresponding International Application No. PCT/US2016/017148; International Filing Date: Feb. 9, 2016 consisting of 6 pages.

Supplementary European Search Report for corresponding Application No. EP 16 75 6057, dated Sep. 26, 2018, 5 pages.

* cited by examiner

BLOOD PUMP FOR TREATMENT OF BRADYCARDIA

CROSS-REFERENCE TO RELATED APPLICATIONS

This application is a Submission Under 35 U.S.C. 371 for U.S. National Stage Patent Application of, and claims priority to, International Application Number PCT/US2016/017148 entitled BLOOD PUMP FOR TREATMENT OF BRADYCARDIA, filed Feb. 9, 2016, which is related to and claims priority from U.S. Provisional Application Ser. No. 62/119,895, filed Feb. 24, 2015, the entirety of all of which are incorporated herein by reference.

FIELD OF THE INVENTION

The present invention relates to ventricular assist devices (VADs).

BACKGROUND OF THE INVENTION

A VAD is a device which is used to assist the heart of a mammalian subject such as a human patient. A typical VAD includes a pump which is implanted in the body of the subject. The pump typically has an inlet connected to a source of blood to be circulated, and an outlet connected to an artery. Most typically, the inlet of the pump is connected to the interior of the left ventricle and the outlet of the pump is connected to the aorta, so that the pump operates in parallel with the left ventricle to impel blood into the aorta. The pump may be a miniature rotary impeller pump having an impeller disposed in a pump housing and driven in rotation by a small electric motor which may be closely integrated with the pump. The motor in turn typically is powered by an implantable power source such as a storage battery with an arrangement for charging the battery from an external power source. The VAD typically includes a control system which controls operation of the power source so as to drive the impeller at a set rotational speed and thus provide constant pumping action.

VADs can be used to assist the heart of subjects suffering from conditions which impair the pumping ability of the heart. Such assistance can be provided permanently, or while the subject awaits a suitable heart transplant. In other cases, the assistance provided by the VAD allows the heart to heal.

BRIEF SUMMARY OF THE INVENTION

One aspect of the invention provides a ventricular assist device or VAD. The VAD desirably includes a rotary pump such as a rotary impeller pump implantable in fluid communication with a ventricle and an artery of a subject to assist blood flow from the ventricle to the artery. The VAD most preferably further includes a pump drive circuit and also preferably includes one or more sensors for sensing one or more electrophysiological signals such as electrogram signals in the subject and providing sensor signals representing the electrophysiological signals. The VAD desirably further includes a signal processing circuit connected to the sensors and the pump drive circuit, the signal processing circuit being operative to detect the sensor signals, and control power supplied to the pump from the pump drive circuit so that the pump runs in a normal sinus rhythm mode with a varying speed synchronized with the cardiac cycle of the subject. As further discussed below, operation in the normal sinus rhythm mode provides improved assistance to the heart.

The signal processing circuit desirably is further operative to determine the presence or absence of a bradycardia arrhythmia, or a slow heart rate such as sinus node or AV node dysfunction (e.g. heart block), based on the sensor signals and to control power supplied to the pump from the pump drive circuit so as to operate the pump in the normal sinus rhythm mode in the absence of a bradycardia arrhythmias and to operate the pump in a modified mode of operation in the presence of a bradycardia arrhythmia. The modified mode may be a constant-speed mode, in which the pump speed does not vary. For example, the pump may run at a different constant speed in the event of third degree or total heart block. The pump may run at a different constant speed in the event of a different arrhythmia such sick sinus syndrome.

DETAILED DESCRIPTION

Figure 1:
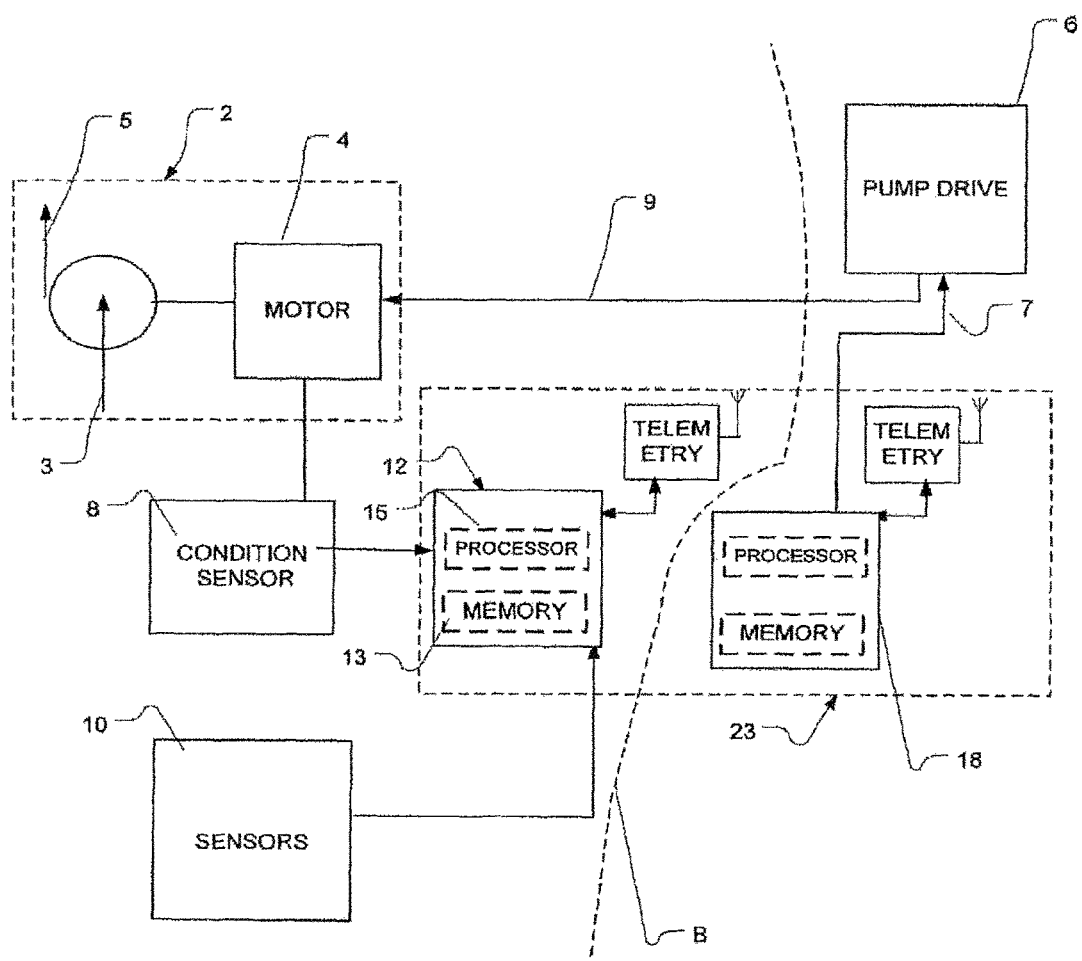
FIG. 1 is a functional block diagram of a VAD in accordance with one embodiment of the invention.

A VAD according to one embodiment of the invention (FIG. 1) includes an implantable rotary pump 2, incorporating a motor 4. As used in this disclosure, the term "rotary pump" refers to a pump which incorporates a pumping element mounted for rotation in a housing. Most typically, the pump 2 is a rotary impeller pump having an impeller mounted within the housing, so that the spinning motion of the impeller transfers momentum to the fluid to be pumped. Although the pump 2 and motor 4 are depicted as separate components for clarity of illustration in FIG. 1, in practice these components can be closely integrated with one another. For example, the impeller of the pump 2 may serve as the rotor of the motor 4. Most typically, the motor 4 is a multi-phase brushless direct current, permanent magnet motor arranged to drive the impeller of the pump 2 at a rotational speed prescribed by the motor driver by means of a motor commutation technique such as trapezoidal commutation. Pump 2 has a fluid inlet 3 and a fluid outlet 5. These components are arranged so that the pump 2 can be implanted within the body of a mammalian subject such as a human patient, with the inlet 3 in fluid communication with a ventricle of the heart, most typically the left ventricle, and with the outlet 5 in fluid communication with an artery, most typically the aorta. For example, the pump 2 may be arranged for implantation outside of the heart, and the inlet and outlet may include conduits that can be surgically connected to the ventricle and the aorta. In other arrangements, the pump 2 is arranged so that they it be implanted within the aorta and ventricle. Implantable pumps are described in detail in U.S. Pat. Nos. 6,264,635; 6,234,772; and 7,699,586 and U.S. Patent Publication No. 2009/

0112312. These patents and published patent applications, which are commonly assigned, are hereby incorporated by reference.

The VAD also includes a pump drive circuit 6. The pump drive circuit 6 may include an electrical storage battery and a motor driver to control the motor. The output of the motor driver is connected by an output connection, such as a cable 9 to the motor 4 of pump 2, so that the motor driver can drive the motor 4 and thus operate the pump 2. The motor driver typically includes semiconductor switching elements which are responsive to control signals applied at a control input 7, so that the current supplied to motor 4 can be controlled. In the particular arrangement depicted, pump drive circuit 6 is mountable outside of the patient's body B and is connected to the motor 4 by conductors which penetrate the skin of the patient. In other arrangements, the pump drive circuit 6 may be implanted within the body and may be connected to an external power source by an inductive coupling or skin-penetrating conductors.

Pump 2 optionally is equipped with a condition sensor 8 such as a speed sensor. For example, the condition sensor may include a back EMF detector operative to detect voltage or current in the stator coils of motor 4 as a measure of motor speed or load.

The VAD also includes a signal processing circuit 23. The signal processing circuit 23 includes an implantable internal module 12 and an external module 18 arranged for mounting outside of the subject's body B. The signal processing circuit 23 is connected to the control input 7 of pump drive circuit 6. Modules 12 and 18 are connected to one another by a suitable signal transmitting arrangement such as radio frequency telemetry transmitting and receiving units 16 so that signals and data can be interchanged between the modules. Modules 12 and 18 include conventional data processing elements such as one or more microprocessors 15 and one or more memory elements 13 arranged to perform the algorithms discussed below. The distribution of hardware elements and software functions between these modules can be varied over a wide range. At one extreme, all of the data processing necessary to perform the algorithm is performed in external control module 18, and the internal module acts essentially as a conduit for data and signals. At the other extreme, all of the hardware and software required to perform the algorithms resides in the internal module 12, and the external module is omitted. The power required to operate the electronic circuitry of the internal module 12 typically is about 3 orders of magnitude less than the power required to drive motor 4. The internal module 12 may be connected to receive power from the alternating current supplied by the pump drive circuit 6 to motor 4. This arrangement is particularly useful where the internal module 12 is physically located at the pump 2. Where the internal module of the signal processing circuit 23 is physically located at the pump 2, it may be desirable to provide magnetic shielding between the coils of the pump motor 4 and the circuitry of the internal module 12. Alternatively, where the internal module 12 is located away from the pump 2, then the signal processing circuitry 23 can receive power from an internal battery such as a primary battery or rechargeable battery.

Figure 2:
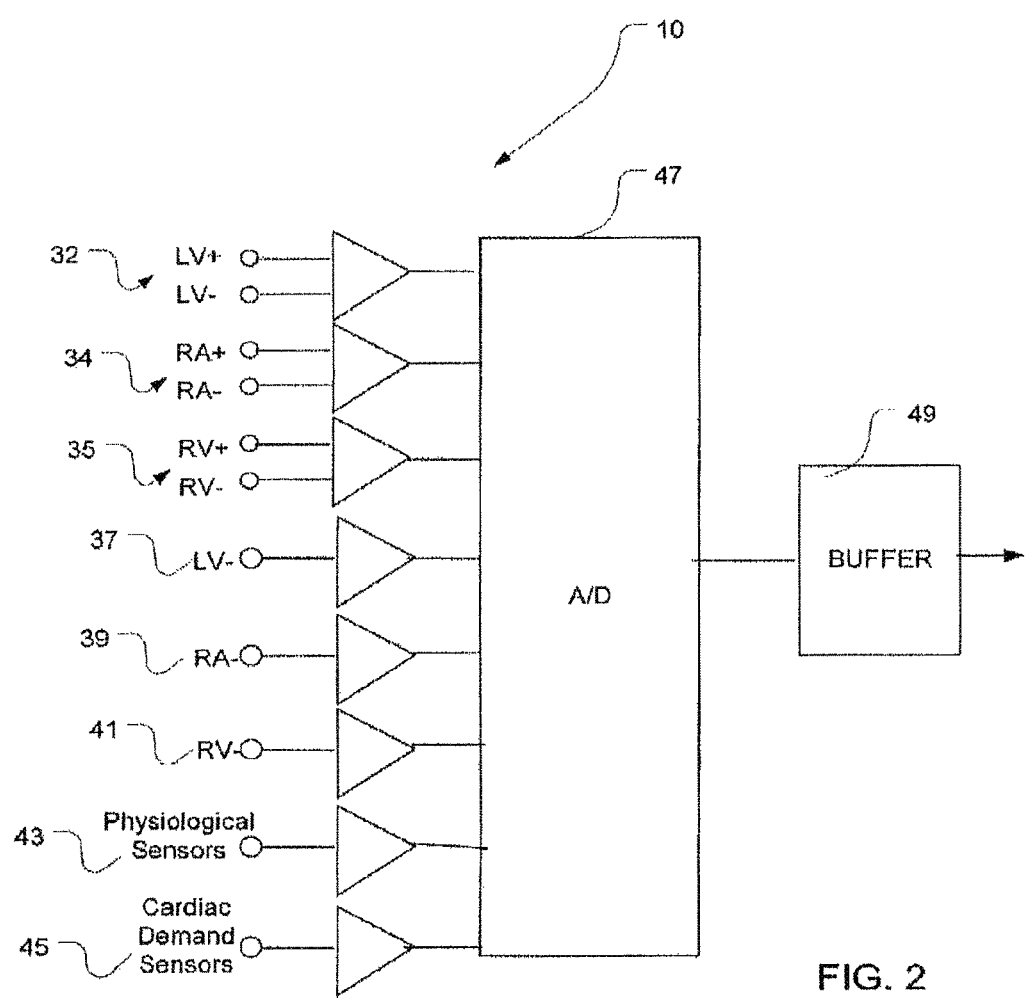
FIG. 2 is a schematic diagram depicting a portion of the VAD of FIG. 1.

The VAD further includes sensors 10 which are connected to the internal module 12 of the signal processing circuit 23. As shown in greater detail in FIG. 2, the sensors include electrogram electrodes such as bipolar electrode pairs 32, 34 and 35 connected to receive signals from the left ventricle, right atrium and right ventricle, respectively. The electrogram sensors further include unipolar electrodes 37, 39 and 41 connected to receive signals from the left ventricle, right atrium and right ventricle. The electrogram electrodes may further include a ground electrode (not shown) connectable to a location remote from the heart to provide a ground reference for use with the signals from the unipolar electrodes. When the VAD is installed, the electrogram electrodes are disposed at appropriate locations on the heart or within the heart of the subject. It is not essential to provide all of the electrogram electrodes shown in FIG. 2. For example, where only the bipolar signals are used for control of the system, the unipolar electrodes may be omitted.

The sensors 10 optionally also include one or more physiological condition sensors 43. The physiological condition sensors 43 can be used to sense and transmit any type of physiological parameter, including but not limited to oxygen concentration, pressure within a vessel or chamber, and temperature. Sensors 10 optionally may also include one or more further sensors 45 arranged to provide a signal representing a parameter related to cardiac demand. For example, the further sensors 45 may include one or more accelerometers arranged to provide signals representing movement of the patient's body B. There is a positive correlation between the amount of movement and cardiac demand.

The various sensors are connected to the internal module 12 of the signal processing circuit 23 through appropriate signal conditioning elements such as an analog to digital converter 47 and buffer memory 49.

Signal processing circuit 23 processes the signals from sensors 10 to determine the phase of the patient's cardiac cycle; to sense the patient's intrinsic heart rate; to determine the patient's metabolic demand; and to detect an arrhythmia such as bradycardia, and sets the mode of operation and speed of the pump 2 accordingly. The signal processing circuit 23 controls frequency of the motor drive signal to the pump 2.

Figure 3:
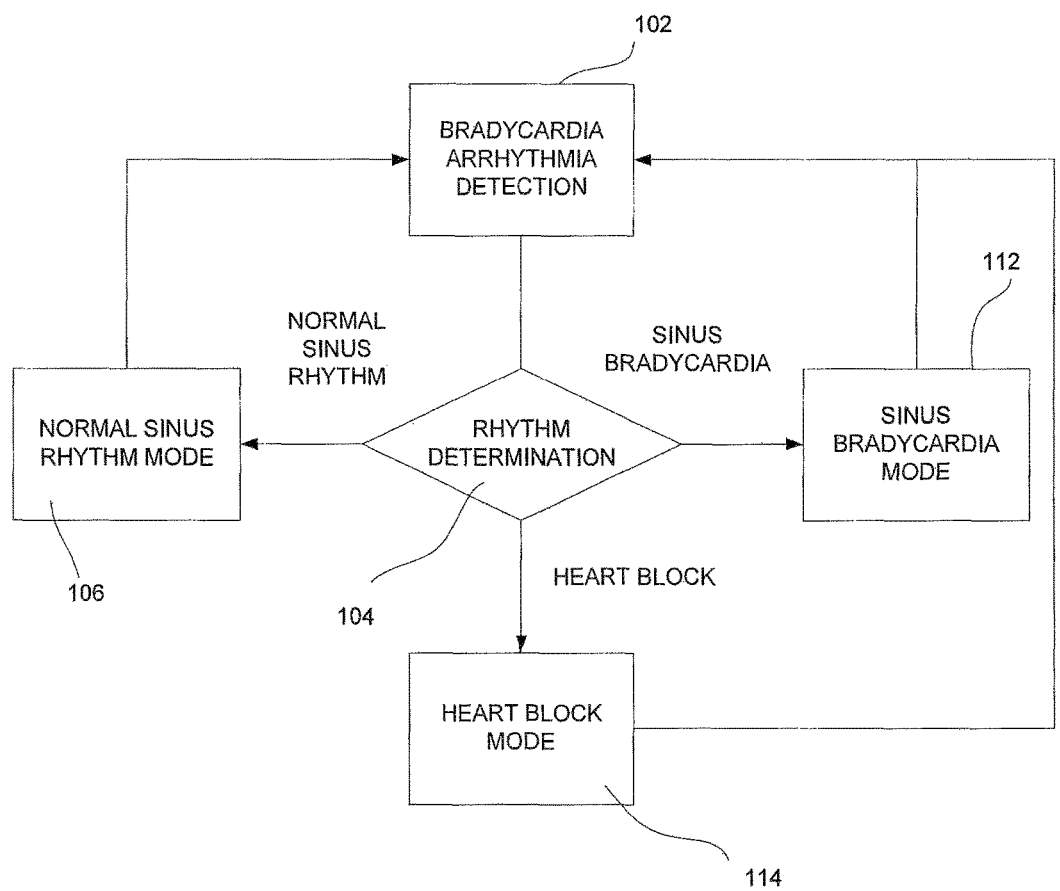
FIG. 3 is a flowchart depicting a portion of an algorithm used in operation of the VAD of FIGS. 1 and 2.

Signal processing circuit 23 repeatedly executes an algorithm as shown in simplified form in FIG. 3. At step 102, a processor executes a bradycardia detection routine using signals acquired from the electrogram electrodes 32, 34, and 35. Bradycardia detection based on electrogram signals are well known in the art and are commonly employed in devices such as implantable pacemakers. Any detection circuit or algorithm routine which is effective to detect bradycardia can be employed. The signals treated in the detection routine may include various sets of signals such as the RA and RV signals from the unipolar or bipolar electrodes.

Figure 4:
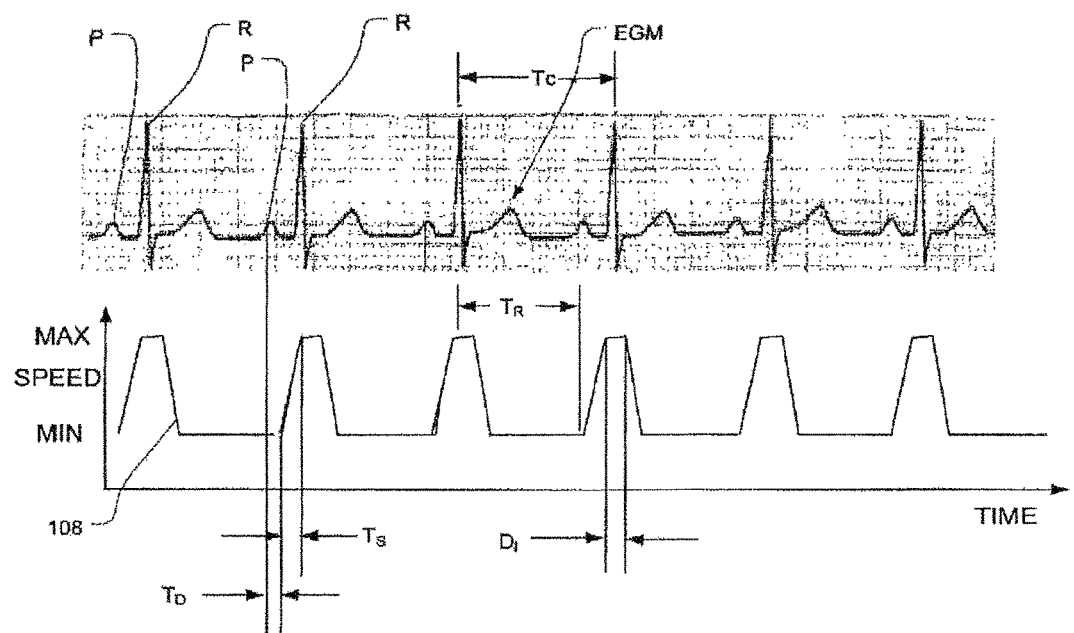
FIG. 4 is a graph of certain signals and variables occurring in operation of the VAD of FIGS. 1-3.

At step 104, the algorithm branches depending on the results of the bradycardia detection. If the detection has determined that the subject's heart is beating in a normal sinus rhythm, with no appreciable arrhythmia, the algorithm moves to step 106 and sets the system to operate in a normal sinus rhythm mode. In this mode, the signal processing circuit 23 actuates pump drive circuit 6 to vary the speed of the pump 2 between a minimum speed and a maximum speed, as depicted by curve 108 (FIG. 4). The pattern of variation in the speed of the pump 2 is synchronized with the intrinsic rhythm of the patient's heart as shown by the electrogram signals EGM so that the variation in speed of the pump 2 has a substantially fixed phase relationship to the intrinsic rhythm of the heart. Most preferably, the pump 2 operates at maximum speed during ventricular systole, when the ventricles contract to expel blood. The EGM curve shown in FIG. 4 is a schematic depiction showing a conventional external electrocardiogram waveform, which represents a composite of the electrical signals in the entire heart. In practice, the actual electrogram signals appearing on electrodes 32-41 (FIG. 2) would be separate signals.

As ventricular systole occurs during the R-wave of the electrogram representing ventricular depolarization, the pump 2 desirably reaches maximum speed at a time close to the timing of the R-wave. The signal processing circuit 23 can use various features of the electrogram signals as the basis for synchronization. A bipolar signal of the left ventricle using epicardial electrodes 32 (FIG. 2) provides exact timing of the ventricular depolarization. The signal processing circuit 23 can simply actuate pump drive circuit 6 to increase the speed of pump 2, each time the left ventricle signal indicates beginning of ventricular depolarization, i.e., at the beginning of the R-wave. However, the mechanical components of pump 2 have inertia and require a finite time to accelerate from minimum speed to maximum speed. This time is referred to herein as the slew time $T_S$ (FIG. 4). To allow for this effect, the signal processing circuit 23 may actuate the pump drive circuit 6 to progressively increase speed of the pump 2 over a period equal to $T_S$.

The signal processing circuit 23 can time the beginning of this period $T_R$ from the R-wave of the preceding cardiac cycle. The cycle time $T_C$ of the cardiac cycle is simply the inverse of the heart rate. Thus, the signal processing circuit 23 can initiate the increase in the pump speed at a time $T_R$ after the R-wave of the preceding cycle, where $T_R=T_C-T_S$. Provided that the heart rate is constant or varying slowly, and that the signal processing circuit 23 updates the heart rate and recalculates $T_C$ frequently, this simple arrangement can yield reasonable synchronization of the pump speed increase with the onset of ventricular systole. The cycle time $T_C$ used in this calculation can be based on a moving average of the cycle time over a few cycles.

Alternatively or additionally, the signal processing circuit 23 can measure the synchronization achieved during each cardiac cycle and advance or retard the initiation of pump acceleration accordingly. For example, if $T_R$ was too short in the preceding cycle, so that the pump 2 reached full speed before the R-wave, the signal processing circuit 23 can increase $T_R$ for the next cycle. Thus, the signal processing circuit 23 can act as a phase-locked loop holding the pump speed waveform in synchronization with the intrinsic cardiac cycle of the patient. In this arrangement, the cyclic variation of pump speed has a fixed phase relationship to the R-wave. In a variant of this arrangement, the measurement of synchronization can be a moving average representing the last few cardiac cycles.

In another arrangement, the signal from the right atrial electrodes is used as a basis for synchronization. The right atrial electrode signal provides exact timing of the initiation of the cardiac excitation process with the P-wave signal. In normal sinus rhythm with no heart block, there is a substantially constant interval from the P-wave to the R-wave in each cardiac cycle. This interval can be estimated from the heart rate or can be determined directly from measurement of the right atrial and left ventricular signals. Thus, the signal processing circuit 23 can time a period $T_D$ (FIG. 4) after each P-wave and initiate pump acceleration at the end of this period. $T_D$ may be selected to equal the P-wave to R-wave interval minus $T_S$. In some instances, $T_S$ may be equal to the P-wave to R-wave interval, in which case $T_D$ may be zero. In this arrangement, the cyclic variation of pump speed has a fixed phase relationship to the P-wave.

Many other features of the electrogram can be used as the basis for synchronization. Software routines for recognizing individual features of an electrogram are known per se, and any such routine can be used in the synchronization scheme.

Functionally, a bipolar waveform with a near field ground may be more ideal for providing timing of atrial and ventricular depolarization because the waveform has a greater differentiated signal. The RA waveform as a bipolar signal may be more useful for providing timing of the atrial depolarization. The RV and LV inputs may be used as bipolar signals for timing analysis for synchronization of pump speed changes.

Synchronizing the VAD with the patient's intrinsic depolarization will allow the pump 2 to operate when it is most advantageous to do so. Cardiac output is greatest during contraction of the atria and ventricles. In a weak or diseased heart, contraction of the chambers, and particularly the left ventricle is when assistance from a VAD is most critical. Therefore timing of the pump 2 with ventricular contraction will provide the optimal assistance to the patient and maximize the therapeutic effect of the VAD. Moreover, operation in the pulsatile mode synchronized to the subject's cardiac cycle can improve efficiency and thus conserve power.

While the synchronization of the pump 2 can be triggered by the actual occurrence of an electrophysiological signal, it is also possible to program the signal processing circuit 23 to anticipate the impending occurrence of a particular EGM waveform. For example, it is well known that each phase of the cardiac cycle should last for approximately the same duration of time in healthy patients. Through a programmed algorithm, the processor could be programmed by methods known in the art to measure and store historical patient data in a memory 13. This memory 13 could be located anywhere within the circuitry of the VAD, or externally.

The data would consist of how long each phase of the cardiac cycle lasts in a given patient in a predetermined time. Measurements take and stored over time can be used to determine through any mathematic or statistical means known, when the next phase of the cardiac cycle should begin in a given patient. This method would allow the processor 15 to instruct the pump drive circuit 6 when to accelerate the pump 2, based on an anticipated EGM waveform. Because atrial and ventricular systole is signaled by the beginning of the P-wave and R-wave respectively, the historical analysis of these phases of the cardiac cycle could be used to predict the onset of systole.

This predictive method of synchronizing the pump 2 with an actual or anticipated EGM waveform is of particular use in patients suffering from left side heart failure. Left side heart failure is a challenging pathology predominantly affecting the left ventricle. Patients with left side failure require assistance in order to maximize the efficiency of the left ventricular contraction. In one embodiment of the present invention, the signal processing circuit 23 will receive EGM waveform signal information from a patient with left sided heart failure. The signal processing circuit 23 will analyze the signal information and determine when an R-wave is occurring or is about to occur. Upon detecting the occurrence or impending occurrence of the complex, the signal processing circuit 23 will instruct the motor 4, through the pump drive circuit 6, to operate in order to drive the pump 2 in synchronism with the patient's own ventricular systole.

The signal processing circuit 23 can set the duration $D_I$ (FIG. 4) of pump operation at maximum speed during each cardiac cycle based on the historical timing of the patient's R-waves. Alternatively, $D_I$ can be set as a fixed proportion of the cardiac cycle time $T_C$. In yet another variant, the signal processing circuit 23 is arranged so that $D_I$, or the routine used to set $D_I$, can be selected by the physician. Typically, $D_f$ is selected so that the pump 2 operates at maximum speed during most or all of ventricular systole.

The maximum speed of the pump 2 or the $D_f$ can be fixed values, or can be set by the signal processing circuit 23 depending on sensed data indicating the current status of the patient. For example, the maximum speed may increase with the heart rate as determined by the electrogram signals from the electrodes, or as determined based on readings from physiological condition sensor 43 (FIG. 2), cardiac demand parameter sensor 45 or some combination of these. Thus, the maximum speed may vary depending on whether the patient is sleeping, awake, and/or exercising. The minimum speed typically is non-zero speed, so that the pump 2 runs continually but speeds up and slows down during each cycle. For example, some rotary impeller pumps utilize hydrodynamic bearings to maintain a pump rotor out of contact with a surrounding pump housing, so that the pump operates with zero wear on the rotor and housing. These hydrodynamic bearings become ineffective when the rotor speed falls below a minimum pump operating speed. When the pump 2 incorporates such bearings, the minimum speed set by the signal processing circuit 23 desirably is set at or above the minimum pump operating speed. The minimum speed can also vary depending on sensed data.

Curve 108 (FIG. 4) depicts the speed variation as a progressive ramp-up from minimum to maximum, followed by operation at maximum, followed by ramp-down to minimum and operation at minimum. However, the pattern of speed variation can be more complex, with the speed continuously varying during the entire cycle. Here again, however, the pattern of speed variation is synchronized with the patient's intrinsic cardiac cycle in the manner described above.

The VAD continues to operate in the normal sinus rhythm mode described above while the signal processing circuit 23 continuously executes bradycardia arrhythmia detection 102 (FIG. 3). So long as the patient remains in normal sinus rhythm, the normal sinus rhythm mode 106 operation continues. However, if a bradycardia condition is detected such as a sinus bradycardia or asystole condition due to a sinus node dysfunction, the program passes to step 112, where the signal processing circuit 23 actuates pump drive circuit 6 to operate the pump 2 in a mode referred to herein as the sinus bradycardia mode 112. In one arrangement, the sinus bradycardia mode 112 is a constant-speed mode in which the pump 2 runs at a constant speed and the pump speed does not vary during the cardiac cycle. Or the sinus bradycardia mode can operate at an asynchronous pulsatile mode. In the sinus bradycardia constant speed mode, signal processing circuit 23 actuates the pump drive circuit 6 to supply power at a constant frequency to the motor 4 of pump 2, so that the pump 2 operates at a constant speed. This speed desirably is less than the maximum speed used during pulsatile operation. While the pump speed is substantially constant during the cardiac cycle, the signal processing circuit 23 optionally can alter the constant speed depending on conditions detected by the physiologic sensor 43.

In another arrangement, the sinus bradycardia mode 112 may be a pulsatile mode in which variation of the pump speed an asynchronous pulsatile mode at a preprogrammed fixed pulse rate or synchronized for sinus beats while providing asynchronous pulsatile flow during extended R-R intervals similar to the operation of a demand pacemaker. The signal processing circuit 23 may include an algorithm to select either a pulsed mode (synchronous or asynchronous) or constant speed mode in response to detecting a sinus bradycardia condition and depending on conditions such metabolic demand.

If the bradycardia arrhythmia detection step 102 detects a bradycardia condition such as an A-V nodal heart-block condition (first degree, second degree or total heart block) the signal processing circuit 23 enters a different mode of operation referred to herein as the heart block mode 114. The heart block mode 114 may be pulsatile and synchronized to the P-wave detected. In these patients, signal processing circuit 23 desirably actuates the pump drive circuit 6 to supply power so that the pump 2 operates at a pulsatile speed.

Alternatively, in the heart-block mode 114, the signal processing circuit 23 actuates the pump drive circuit 6 to operate the pump 2 in a pulsatile mode which is not synchronized to the cardiac cycle and at a preprogrammed rate.

While the VAD is in sinus bradycardia mode 112 or in heart block mode 114, the signal processing circuit 23 continually executes the bradycardia arrhythmia detection routine 102. If routine 102 detects a return to normal sinus rhythm, indicating that the arrhythmia has passed, the normal sinus rhythm mode 106 is restored.

A VAD according to a further embodiment incorporates a pacemaker 100, which in this embodiment is a single or dual chamber pacemaker. The pacemaker is designed to treat various conduction conditions associated with bradycardia.

Figure 5:
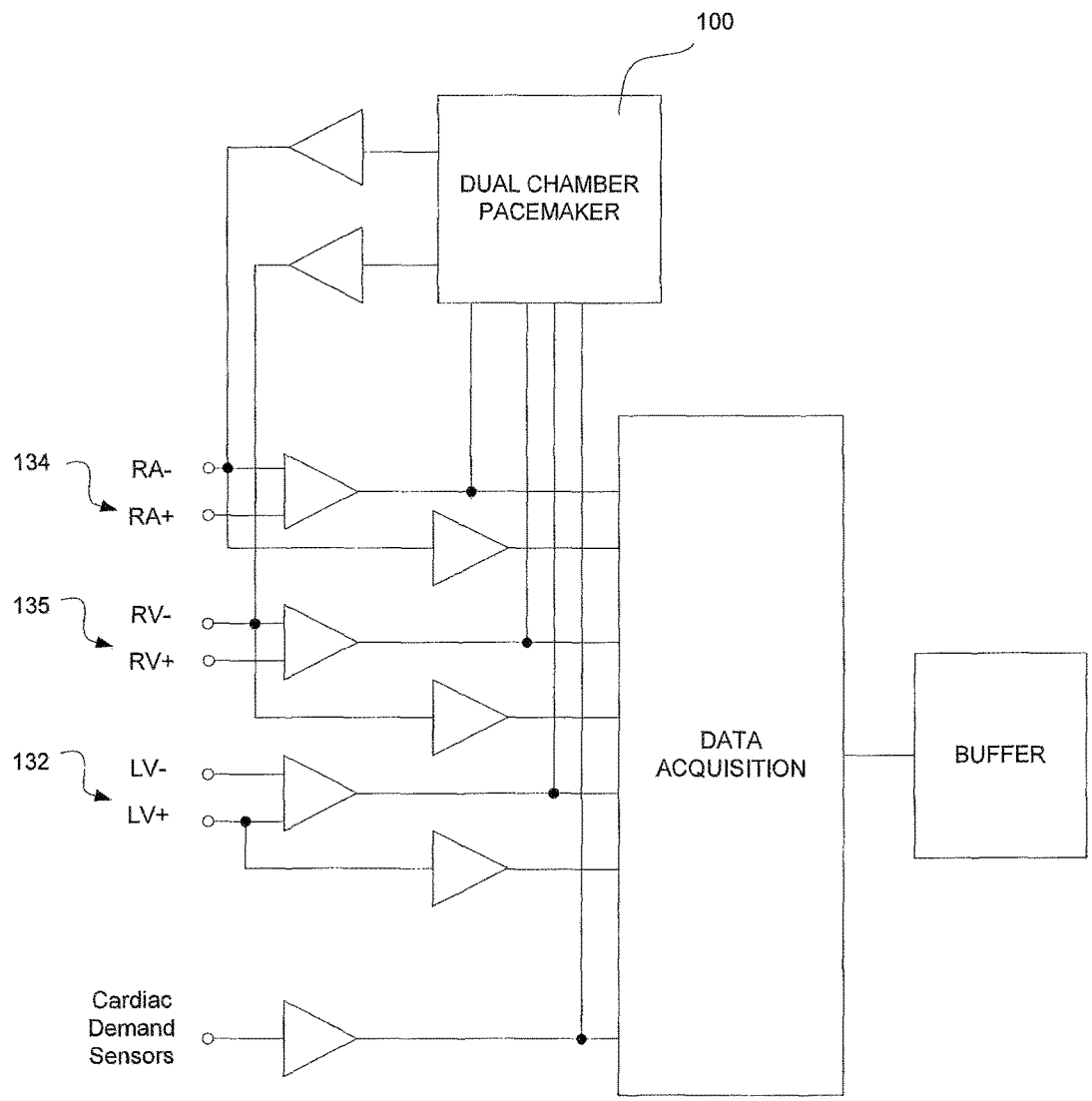
FIG. 5 is a diagram similar to FIG. 2 but depicting a portion of a VAD in accordance with a further embodiment of the invention.

As seen in FIG. 5, pacemaker 100 has output connections connected to the ventricular electrodes 134 and 135 used for sensing the electrogram signal. In this arrangement, the pacemaker 100 incorporates an internal control circuit (not shown) so that the pacemaker can apply pacing signals to the heart through the electrodes. In a further variant, the functions of the pacemaker 100 can be performed by the same signal processing circuit 23 used to operate the pump 2. A pacemaker combined with a VAD could provide for optimized pump synchronization and control features discussed above. The pacemaker 100 helps to restoring the R-R interval timing for patients who have conduction problems resulting in bradycardia conditions described above.

In still other embodiments, the bradycardia arrhythmia detection and response discussed above can be applied in VADs having pumps other than rotary pumps.

While various elements have been described above as individual components depicted in functional block diagrams, these elements can be combined with one another. Conversely, elements shown as unitary elements in the functional block diagrams discussed above can be separated into separate elements. Also, the features described above with reference to different embodiments of the invention can be combined with one another.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A ventricular assist device comprising:
a rotary pump configured to be implantable in fluid communication with a ventricle and an artery of a subject to assist blood flow from the ventricle to the artery;

a pump drive circuit for applying power to the pump;
a pump drive circuit to control the speed of the pump;
one or more sensors for sensing one or more electrogram signals in a patient;
a signal processing circuit in communication with the sensors and the pump drive circuit, the signal processing circuit being configured to receive the electrogram signals and:
  determine an impending onset or absence of a bradycardia arrhythmia based on the electrogram signals from the sensors;
  during the impeding onset of a bradycardia arrhythmia, determine the impending onset of sinus bradycardia or heart block;
  control power supplied to the pump from the pump drive circuit so as to control the speed of the pump and:
  operate the pump in a normal sinus rhythm mode in the absence of an arrhythmia;
  operate the pump in a first modified mode of operation during the impending onset of heart block or sinus bradycardia.

2. The device of claim 1 wherein the pump is a rotary impeller pump.

3. The device of claim 1, wherein the signal processing circuit is configured to adjust the varying speed responsive to a condition of the subject.

4. The device of claim 3, wherein the signal processing circuit adjusts the varying speed in accordance with electrophysiological signals received by the circuit from the sensors.

5. The device of claim 1, wherein the signal processing circuit is configured to control power supplied to the pump so that the varying speed has a substantially fixed phase relationship with the P-wave of the subject's cardiac cycle.

6. The device of claim 1, wherein the signal processing circuit is configured to control power supplied to the pump so that the varying speed has a substantially fixed phase relationship with the R-wave of the subject's cardiac cycle.

7. The device of claim 1, wherein the device further comprises a pacemaker configured to providing a pacing function for conditions of bradycardia.

8. The device of claim 1, wherein the electrophysiological signals include RA, RV and LV waveforms.

9. The device of claim 8, wherein the RA, RV and LV waveforms include at least one bipolar signal.

10. The device of claim 1, wherein the circuit is configured to detect a sinus bradycardia and the first modified mode of operation includes a sinus bradycardia mode different from the normal sinus rhythm mode.

11. The device of claim 10, wherein the sinus bradycardia mode includes a non-pulsatile mode, and wherein the pump runs in a non-pulsatile manner.

12. The device of claim 10, wherein the sinus bradycardia mode includes a sinus bradycardia pulsatile mode different from the normal sinus rhythm mode.

13. The device of claim 1, wherein the circuit is configured to detect a heart block arrhythmia and the second modified mode of operation is a heart block arrhythmia mode different from the normal sinus rhythm mode.

14. The device of claim 13, wherein the heart block arrhythmia mode includes a non-pulsatile mode wherein the pump runs in a non-pulsatile manner.

15. The device of claim 13, wherein the heart block mode includes a pulsatile mode wherein the pump runs in a pulsatile manner unsynchronized with the cardiac cycle of the subject.

* * * * *